(12) United States Patent
Gephart

(10) Patent No.: US 8,984,720 B2
(45) Date of Patent: Mar. 24, 2015

(54) TENSIONING INSTRUMENT AND METHOD

(71) Applicant: Pioneer Surgical Technology, Inc., Marquette, MI (US)

(72) Inventor: Matthew P. Gephart, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 13/730,597

(22) Filed: Dec. 28, 2012

(65) Prior Publication Data

US 2013/0167334 A1     Jul. 4, 2013

Related U.S. Application Data

(60) Provisional application No. 61/581,029, filed on Dec. 28, 2011.

(51) Int. Cl.
*A61B 17/88*     (2006.01)

(52) U.S. Cl.
CPC ......... *A61B 17/8861* (2013.01); *A61B 17/8869* (2013.01)
USPC ........... 24/69 R; 24/115 R; 24/133; 24/134 R

(58) Field of Classification Search
USPC ............................ 24/69 R, 115 R, 133, 134 R
See application file for complete search history.

(56) References Cited

U.S. PATENT DOCUMENTS

| | | | |
|---|---|---|---|
| 1,988,534 A * | 1/1935 | Abbott | 254/253 |
| 2,002,977 A * | 5/1935 | Carr | 73/862.392 |
| 4,050,464 A | 9/1977 | Hall | |
| 5,312,410 A * | 5/1994 | Miller et al. | 606/86 R |
| 5,395,374 A | 3/1995 | Miller et al. | |
| 5,415,658 A | 5/1995 | Kilpela et al. | |
| 5,449,361 A | 9/1995 | Preissman | |
| 5,456,722 A | 10/1995 | McLeod et al. | |
| 5,568,865 A | 10/1996 | Mase et al. | |
| 5,569,253 A | 10/1996 | Farris et al. | |
| 5,702,399 A | 12/1997 | Kilpela et al. | |

(Continued)

FOREIGN PATENT DOCUMENTS

| | | |
|---|---|---|
| AU | 743254 B | 1/2002 |
| TW | 314764 Y | 9/1997 |

(Continued)

*Primary Examiner* — Robert J Sandy
*Assistant Examiner* — David Upchurch
(74) *Attorney, Agent, or Firm* — Fitch, Even, Tabin & Flannery LLP

(57) ABSTRACT

In one aspect, a tensioning instrument for a securing device, such as surgical cable, is provided having a pretensioning mechanism configured to allow a predetermined preload tension to be applied to the cable and a tensioning mechanism operable to increase the tension in the cable by predetermined amount in excess of the preload tension applied by the pretensioning ,mechanism. The tensioning device has a first actuator operatively coupled to the pretensioning mechanism and is configured permit a predetermined preload tension to be applied to the cable. The tensioning device also has a second actuator different than the first actuator which is operatively coupled to the tensioning mechanism. The second actuator may be moved between an open position and a locked position to cause the tensioning mechanism to increase the tension in the cable by the predetermined amount in excess of the preload tension, if any.

27 Claims, 17 Drawing Sheets

(56) References Cited

U.S. PATENT DOCUMENTS

| | | | |
|---|---|---|---|
| 5,902,305 A | 5/1999 | Beger et al. | |
| 5,935,130 A * | 8/1999 | Kilpela et al. | 606/74 |
| 5,935,133 A | 8/1999 | Wagner et al. | |
| 6,077,268 A | 6/2000 | Farris et al. | |
| 6,086,590 A | 7/2000 | Margulies et al. | |
| 6,099,527 A | 8/2000 | Hochschuler et al. | |
| 6,277,120 B1 | 8/2001 | Lawson | |
| 6,378,289 B1 * | 4/2002 | Trudeau et al. | 606/103 |
| 6,387,099 B1 | 5/2002 | Lange et al. | |
| 6,398,787 B1 | 6/2002 | Itoman | |
| 6,475,220 B1 | 11/2002 | Whiteside | |
| 7,494,461 B2 * | 2/2009 | Wells et al. | 600/104 |
| 2002/0072753 A1 | 6/2002 | Cohen | |
| 2002/0177861 A1 * | 11/2002 | Sugiyama et al. | 606/151 |
| 2004/0138666 A1 * | 7/2004 | Molz et al. | 606/74 |
| 2004/0199169 A1 | 10/2004 | Koons et al. | |
| 2005/0171547 A1 | 8/2005 | Aram | |
| 2005/0177179 A1 | 8/2005 | Baynham et al. | |
| 2006/0089646 A1 | 4/2006 | Bonutti | |
| 2006/0167464 A1 | 7/2006 | Allen et al. | |
| 2008/0195145 A1 | 8/2008 | Bonutti et al. | |
| 2008/0287951 A1 | 11/2008 | Stoneburner et al. | |
| 2009/0043316 A1 * | 2/2009 | Durgin et al. | 606/142 |
| 2009/0054933 A1 * | 2/2009 | Mickiewicz et al. | 606/86 A |
| 2009/0171402 A1 | 7/2009 | Dell'Oca | |
| 2010/0042106 A1 | 2/2010 | Bryant et al. | |
| 2010/0057091 A1 | 3/2010 | Oosterom | |
| 2010/0094362 A1 * | 4/2010 | Lutze et al. | 606/86 R |
| 2010/0179595 A1 | 7/2010 | Bao et al. | |
| 2010/0305571 A1 | 12/2010 | Pratt et al. | |
| 2010/0318137 A1 | 12/2010 | Stucki et al. | |
| 2011/0112537 A1 * | 5/2011 | Bernstein et al. | 606/74 |
| 2012/0215224 A1 | 8/2012 | Songer | |

FOREIGN PATENT DOCUMENTS

| | | |
|---|---|---|
| WO | 9428812 | 12/1994 |
| WO | 0234120 A2 | 5/2002 |
| WO | 2006088452 A | 8/2006 |

* cited by examiner

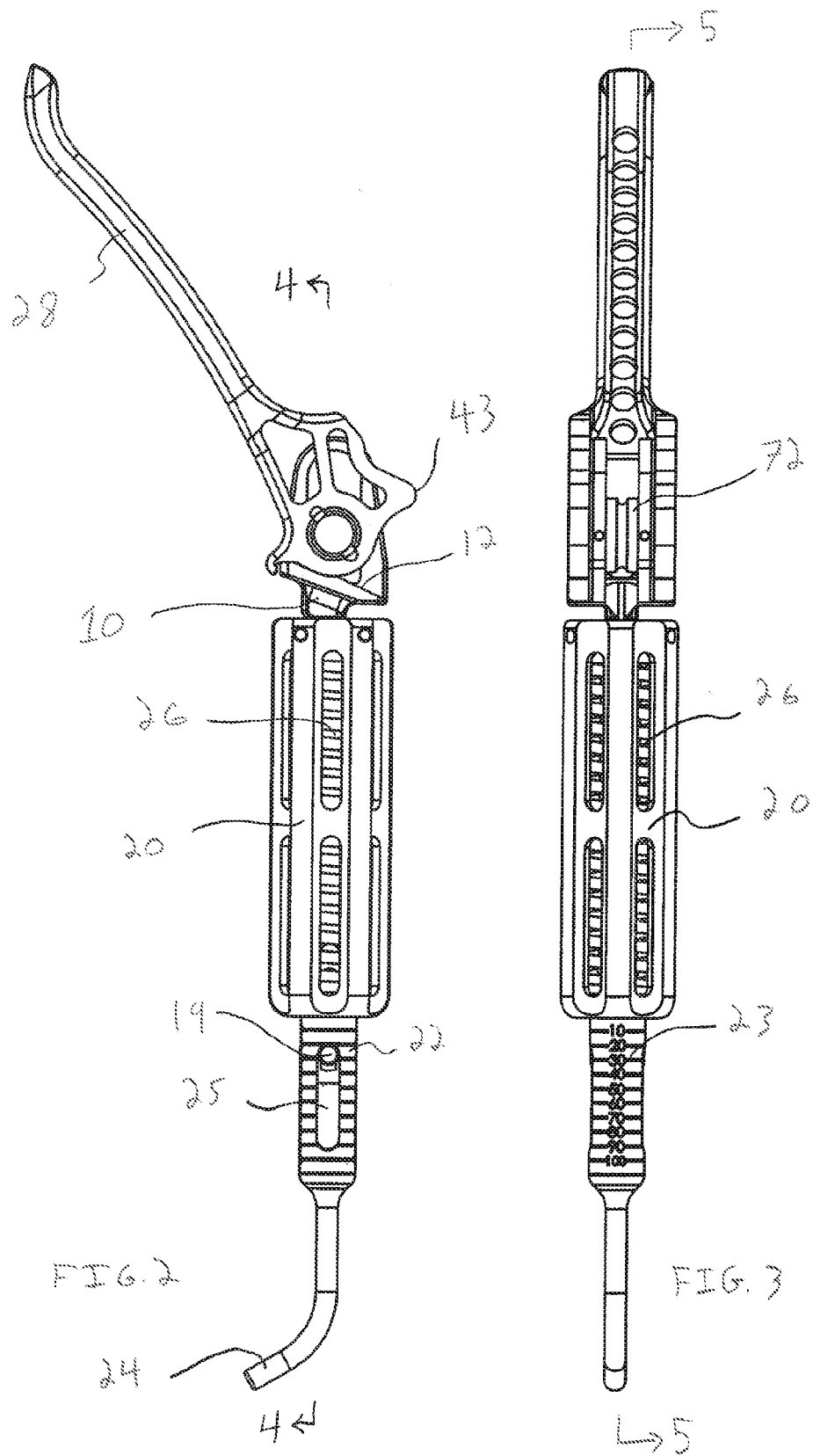

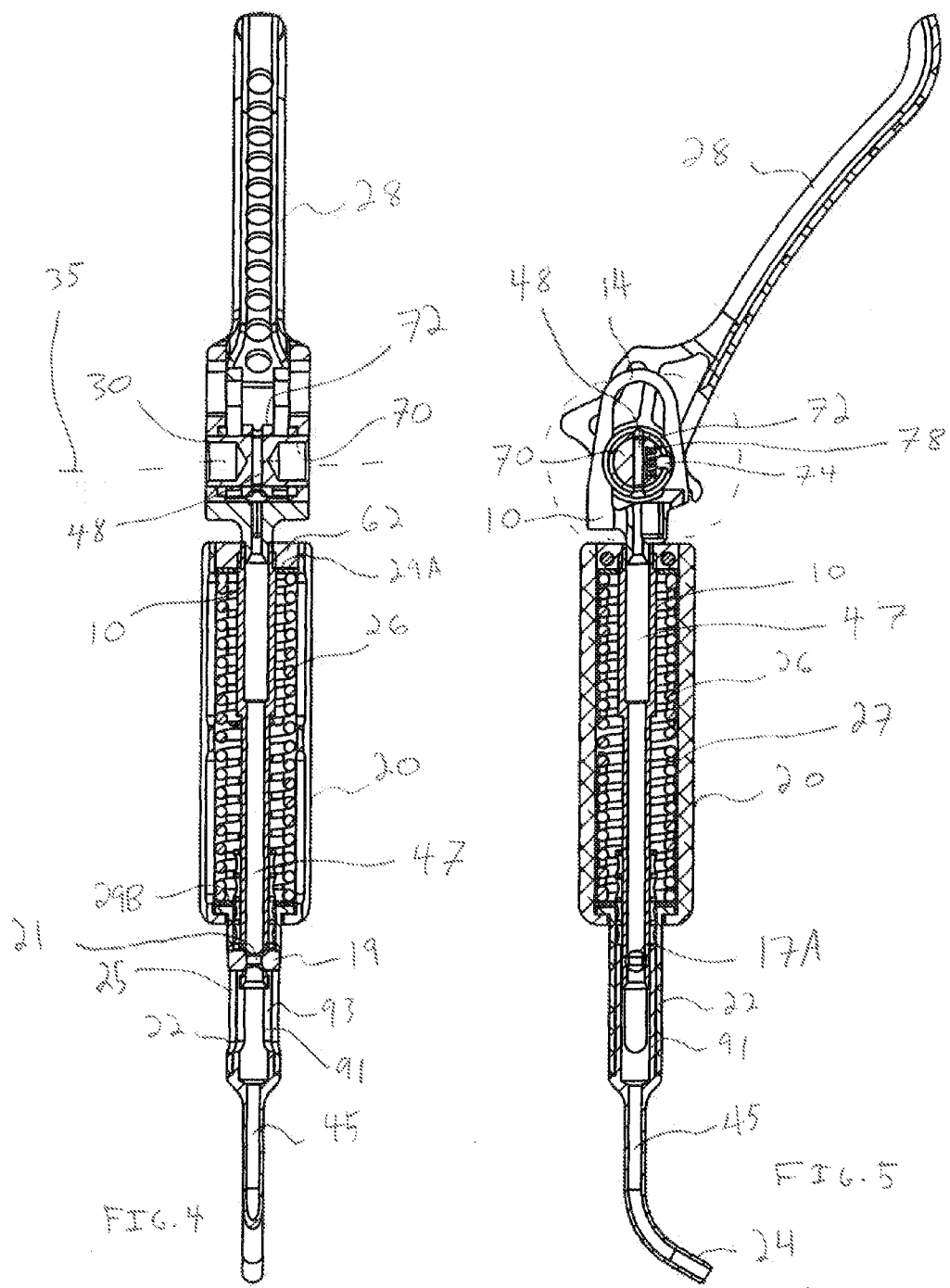

TENSIONING INSTRUMENT AND METHOD

CROSS-REFERENCE TO RELATED APPLICATION

This application claims the benefit of U.S. Provisional Patent Application No. 61/581,029, filed Dec. 28, 2011, which is hereby incorporated by reference in its entirety.

FIELD OF THE INVENTION

The present invention relates generally to apparatus and methods for tensioning securing devices and, more specifically, to apparatus and methods for tensioning securing devices in a variety of medical procedures.

BACKGROUND

Securing devices, such as cables or wires, are often used in orthopedic surgery for securing bones in place and for fastening implants to the bones. In one type of procedure, a cable having a pair of opposite ends is positioned around a pair of bones. The cable has a connector at one end, and the other end is inserted into the connector to form a loop of the cable around the bones. As used herein, the term bone may refer to a bone, a bone fragment, or a portion of a bone.

A tensioning instrument may be used to apply tension to the cable and constrict the loop of cable about the bones and implant. Tensioning instruments may be very complex and include, for example, a cable locking mechanism, a cable tensioning mechanism, a detachable re-tension mechanism, and a tension scale. Some prior tensioning instruments use different mechanisms to provide each of these features, which increases the cost and size of the tensioning instrument.

Some surgeries require multiple cables to be implanted that each require tensioning. One prior tensioning instrument that may be used in such a surgery is a pistol-type tensioner having a detachable tip for holding tension in each surgical cable. During surgery, the tensioning instrument is used to apply a desired amount of tension to a first cable, the tip is engaged to the cable to hold tension in the cable construct, the tip is detached, a new tip is connected to the tensioning instrument, and the tensioning instrument is moved to the next cable. This procedure is repeated until all of the cables have been tensioned. Connectors on the cables are then crimped to secure the cables on the bones. One problem with this approach is that once a cable has been tensioned and the tensioning instrument detached from the tip, the tension in the cable may change, for example, due to tensioning of another cable around nearby bones. The operator would not be aware of the change in tension unless the tensioning instrument is reconnected to the first tip and used to gauge the tension in the first surgical cable.

SUMMARY

In accordance with one aspect of the present invention, a tensioning instrument is provided that enables a user to quickly and easily apply a desired amount of tension to a securing device such as a surgical cable. The tensioning instrument has a pretensioning mechanism that allows a predetermined preload tension to be applied to the cable and a tensioning mechanism operable to increase the tension in the cable in excess of the preload tension applied by the pretensioning mechanism. The tensioning instrument thereby permits a user to apply a predetermined amount of tension to the surgical cable using the tensioning mechanism as well as utilize an optional preload if cable tension greater than the predetermined amount provided by the mechanism is desired. The pretensioning mechanism may be adjusted to set a desired preload before the tensioning instrument is connected to the surgical cable, or after the tensioning instrument has been connected to the surgical cable and the predetermined amount of tension has been applied by the tensioning mechanism. As discussed in greater detail below, this functionality allows a user to configure a plurality of tensioning instruments to provide a common amount of tension to a plurality of surgical cables as well as make in-situ adjustment of the tension applied to each surgical cable once the tensioning instruments have been connected to the cable by simply adjusting the pretensioning mechanism of the respective tensioning instrument.

In one form, the tensioning instrument has a first actuator operatively coupled to the pretensioning mechanism that is configured to be moved between an initial position where the predetermined preload tension applied to the cable by the pretensioning mechanism is a nominal amount and a preloading position where the predetermined preloading tension applied by the pretensioning mechanism is greater than the nominal amount. The tensioning instrument preferably has indicia including a scale on an outer surface of the tensioning instrument adjacent the first actuator that permits measurement of the preload tension to be applied by the pretensioning mechanism based upon the position of first actuator.

The tensioning instrument also includes a second actuator different from the first actuator that is operatively coupled to the tensioning mechanism. The second actuator is movable between open and locked positions which causes the tensioning mechanism to increase the tension in the cable by the predetermined amount provided by the tensioning mechanism. The predetermined amount of tension applied by the tensioning mechanism may be tension in excess of the preload tension applied by the pretensioning mechanism. For example, if the predetermined amount of tension applied by the tensioning mechanism is forty newtons (40 N), and first actuator is in the initial position so that the preload tension is zero newtons (0 N), moving the second actuator to the locked position will cause the tensioning mechanism to increase the tension in the cable to forty newtons. The use of first and second actuators to independently control the preload and tension applied to the cable provides an efficient and easy to use instrument for applying a desired amount of tension to the surgical cable.

In accordance with another aspect of the present invention, a tensioning instrument for tensioning a surgical cable is provided that has fewer components, is more compact, and is easier to use than prior tensioning instruments. The tensioning instrument includes a guide, a support slidably connected to the guide, and a biasing member disposed between the guide and the support that is configured to bias the support away from the guide. The tensioning instrument further includes a locking mechanism configured to be connected to the cable, an actuator connected to the locking mechanism and pivotal relative to the support between open and locked positions, and engagement surfaces of the actuator and guide. Pivoting the actuator between the open and locked positions engages the engagement surfaces and shifts the support toward the guide which compresses the biasing member and applies a tensioning force to the cable when the locking mechanism is fixed to the cable. In this manner, the tensioning instrument provides both locking and tensioning functionality in an integrated mechanism rather than separate locking and tensioning mechanisms as in some prior tensioning instruments. This approach reduces the number of components of the tensioning instrument which reduces the weight and cost of the instrument. Further, by using fewer components, multiple tensioning instruments can be supplied in a surgical set to simplify tensioning of multiple cables and eliminate the need for re-tension mechanisms.

In one form, the actuator is rigidly connected to the locking mechanism and the instrument has a pivot connection between the locking mechanism and the support. The pivot connection permits the locking mechanism to pivot relative to the support with pivoting of the actuator between the open and locked positions. Pivoting the locking mechanism reconfigures the locking mechanism to the locked configuration and fixes the locking mechanism to the cable. Thus, pivoting the actuator between the open and locked positions both tensions the cable and fixes the locking mechanism to the cable. This dual functionality provides substantial time savings compared to some traditional cable tensioning instruments that require separate procedures to fix the instrument to the cable and tension the cable.

In another aspect of the present invention, a method of tensioning a cable is provided that permits the cable to be quickly tensioned around one or more bone portions. The method includes feeding an end portion of the cable into a distal end portion of a tensioning instrument, fixing a locking mechanism of the instrument to the cable, and pivoting an actuator connected to the locking mechanism from an open position toward a locked position. The method further includes engaging surfaces of the actuator and a support of the instrument with pivoting of the actuator to shift the support toward the distal end portion of the instrument. Shifting of the support toward the distal end portion compresses a biasing member of the instrument and applies a tensioning force to the cable. The method thereby permits the tensioning instrument to be connected to the cable, the locking mechanism fixed to the cable, and tension applied to the cable with fewer steps than some previous cable tensioning procedures.

BRIEF DESCRIPTION OF THE DRAWINGS

FIG. 2 is a side elevational view of the tensioning instrument of FIG. 1 showing a curved distal end of the tensioning instrument;

FIG. 3 is an end elevational view of the tensioning instrument of FIG. 1 showing a cable tension scale of the instrument;

FIG. 4 is a cross-sectional view taken across line 4-4 in FIG. 2 showing a cable passageway extending through a center of the instrument;

FIG. 5 is a cross-sectional view taken across line 5-5 in FIG. 3 showing a through aperture of a locking mechanism of the tensioning instrument aligned with the cable passageway when a lever of the tensioning instrument is in the open position;

DETAILED DESCRIPTION

Figure 1:
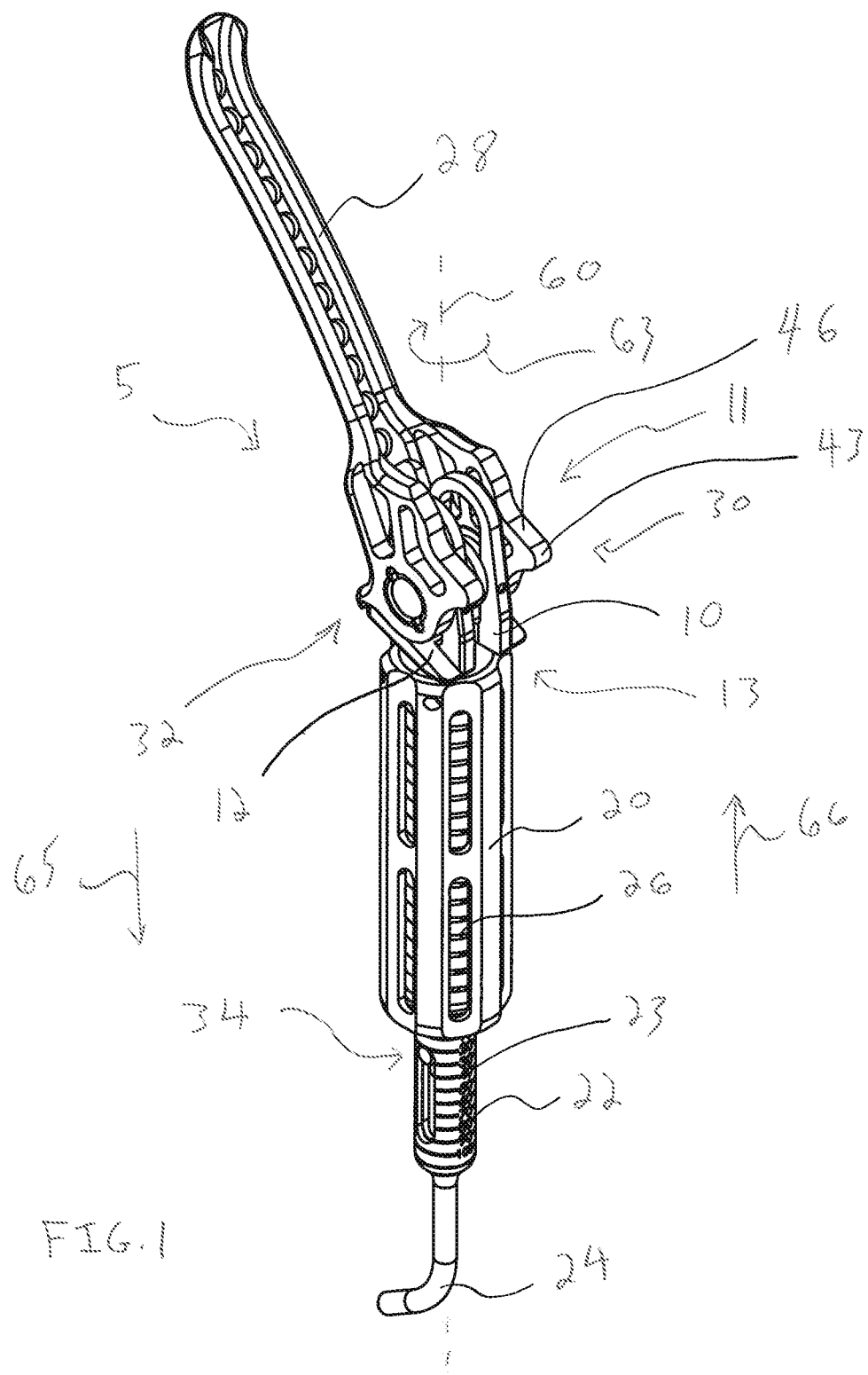
FIG. 1 is a perspective view of a tensioning instrument in accordance with the present invention showing a handle of the tensioning instrument in an open or unlocked position.
Figure 12:
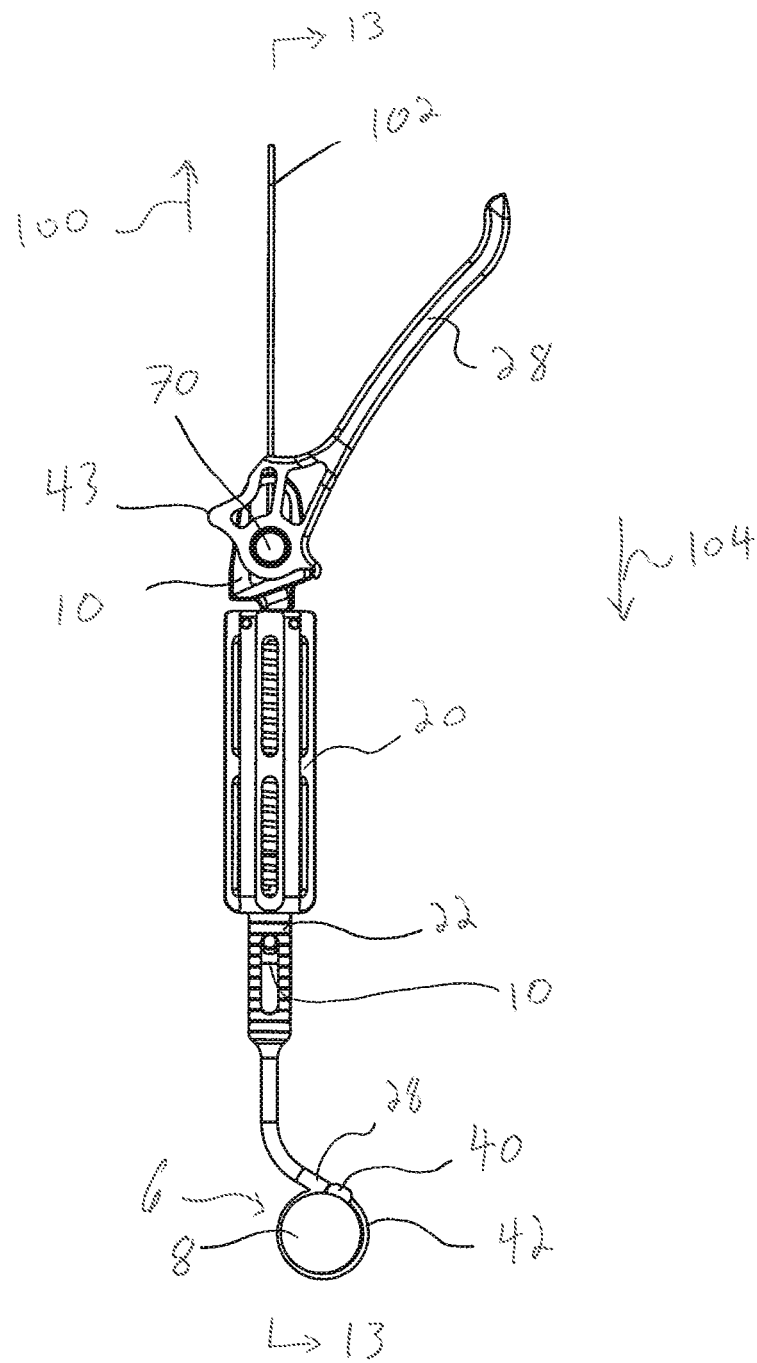
FIG. 12 is a schematic view of the tensioning instrument of FIG. 1 showing the distal end portion of the tensioning instrument engaged with a connector of a cable looped around a bone and a leading end of the cable advanced outward from a proximal end portion of the instrument.
Figure 13:
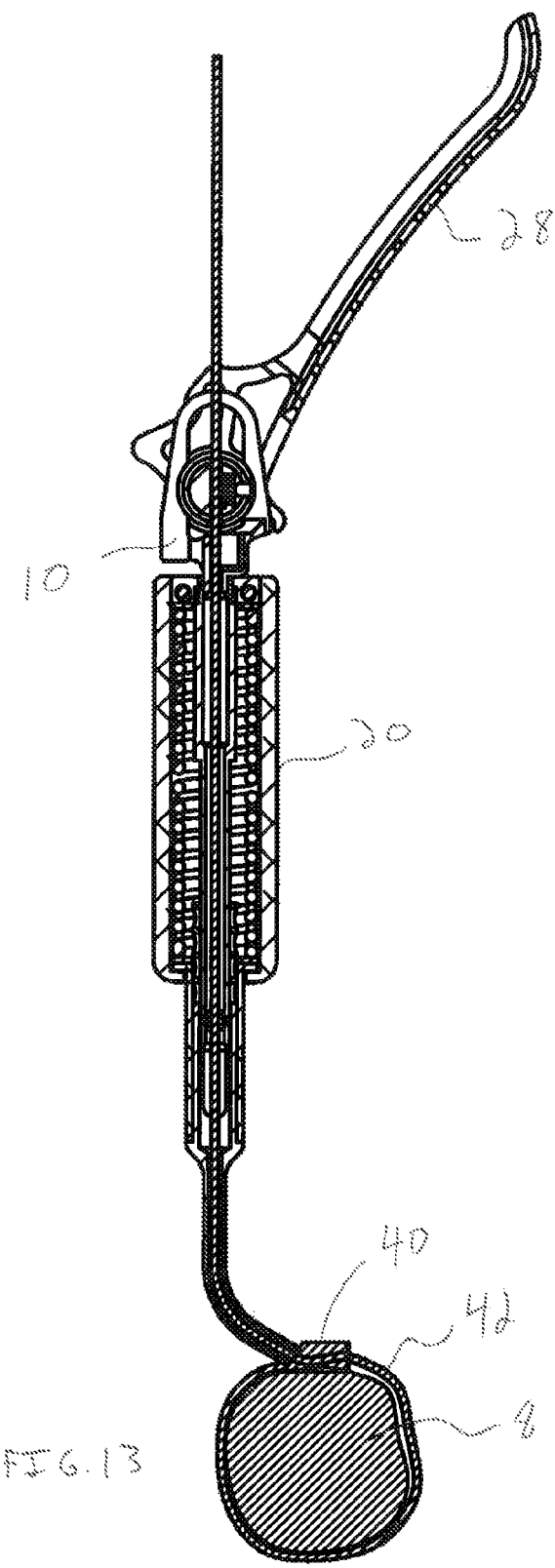
FIG. 13 is a cross-sectional view of the tensioning instrument and cable of FIG. 12.

With reference to FIGS. 1 and 12, a tensioning instrument 5 is provided for tensioning a securing device, such as a cerclage cable 6 about a bone 8. The cerclage cable construct may include a cable 40 and a cerclage connector 42 disposed at one end of the cable for locking the cerclage cable 40 about the bone 8. The instrument 5 generally has a tensioning mechanism 11 with a first actuator, such as a lever 28, which is moved between an open position (see e.g., FIG. 12) and a locked position (see e.g., FIG. 16) to apply a predetermined amount of tension to the cable 40. The instrument 5 also has a pretension mechanism 13 with a second actuator, such as handle 20, which may be moved between an initial position (see FIG. 12) and a preload position (see FIG. 18) to cause the pretension mechanism 13 to apply a desired amount of pretension to the cable 40. The pretension mechanism 13 may be operated independently of the tensioning mechanism 11 so that the desired amount of pretension can be applied before, during, or after the lever 28 is pivoted between the open and locked positions. Further, the tensioning mechanism 11 preferably includes a locking mechanism 30 and a tension measurement device 34. The instrument 5 thereby advantageously provides a tensioning mechanism 11, pretension mechanism 13, and tension measurement device 34 in one compact and easy to use device.

Figure 6:
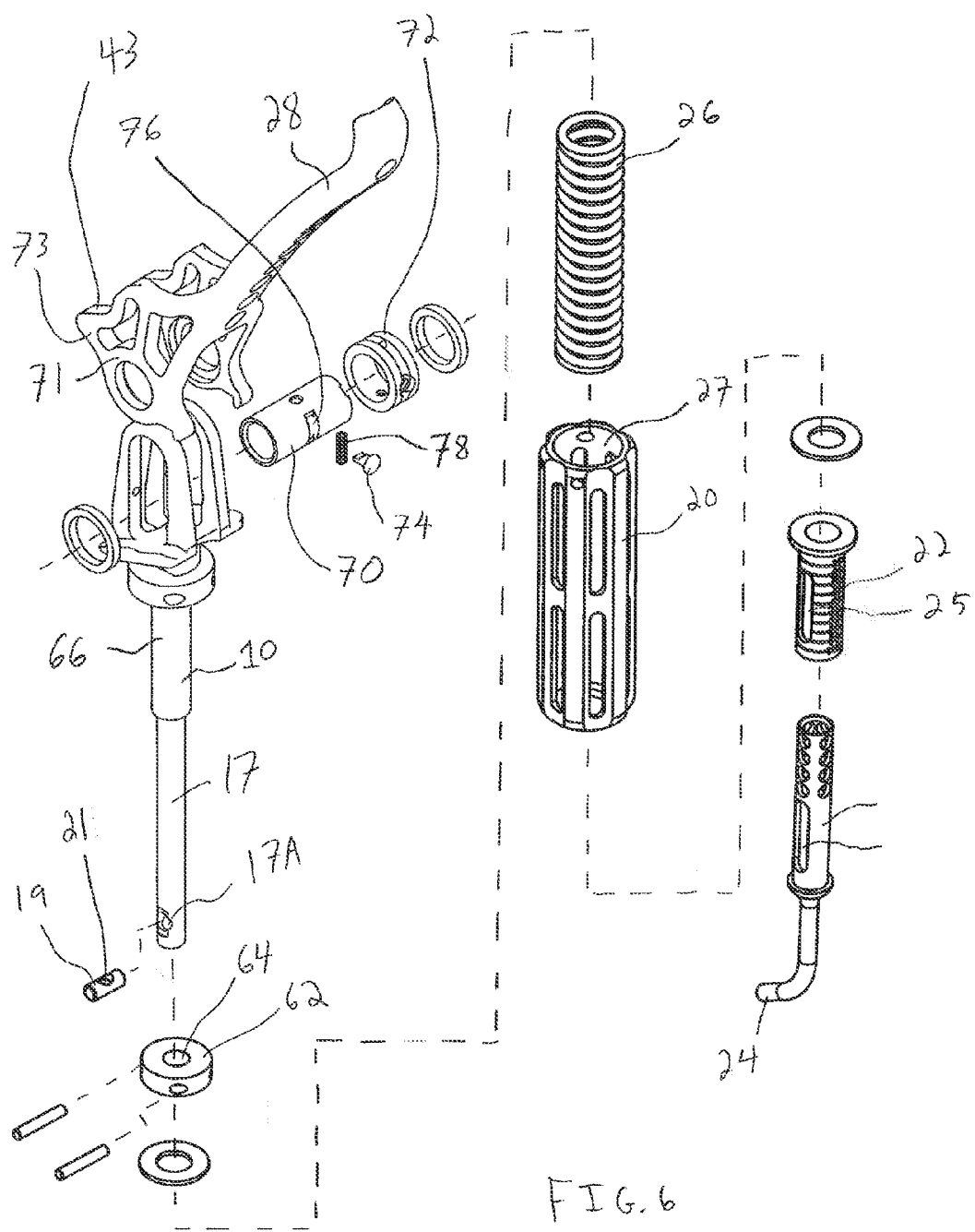
FIG. 6 is an exploded schematic view of the tensioning instrument of FIG. 1 showing components of the locking mechanism and tensioning mechanism of the instrument.
Figure 7:
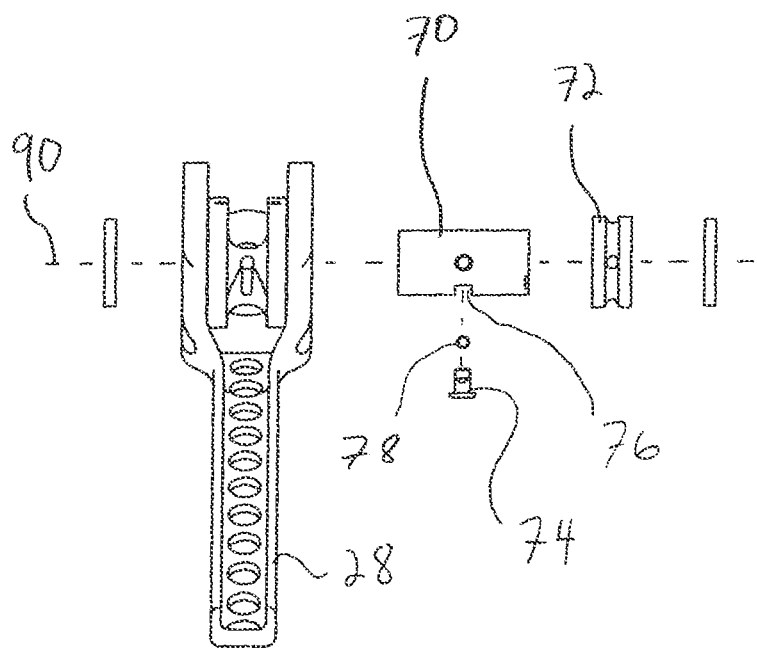
FIG. 7 is a top plan view of the locking mechanism components of FIG. 6.
Figure 8:
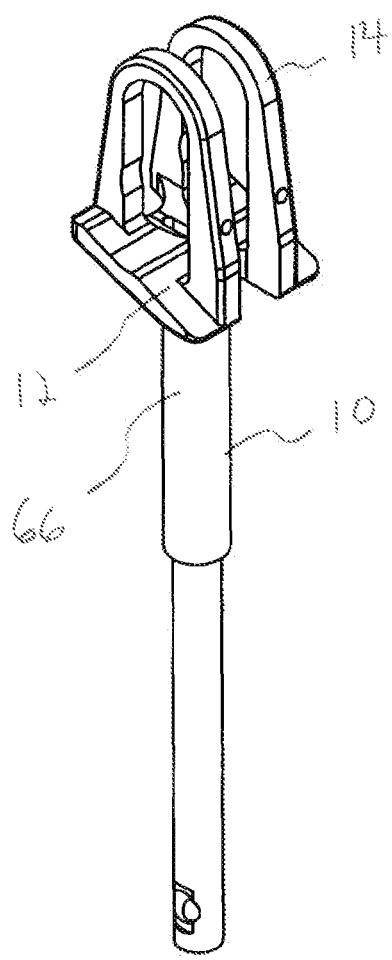
FIG. 8 is a perspective view of an inner body of the tensioning instrument of FIG. 1 showing retention structures of the inner body.
Figure 9:
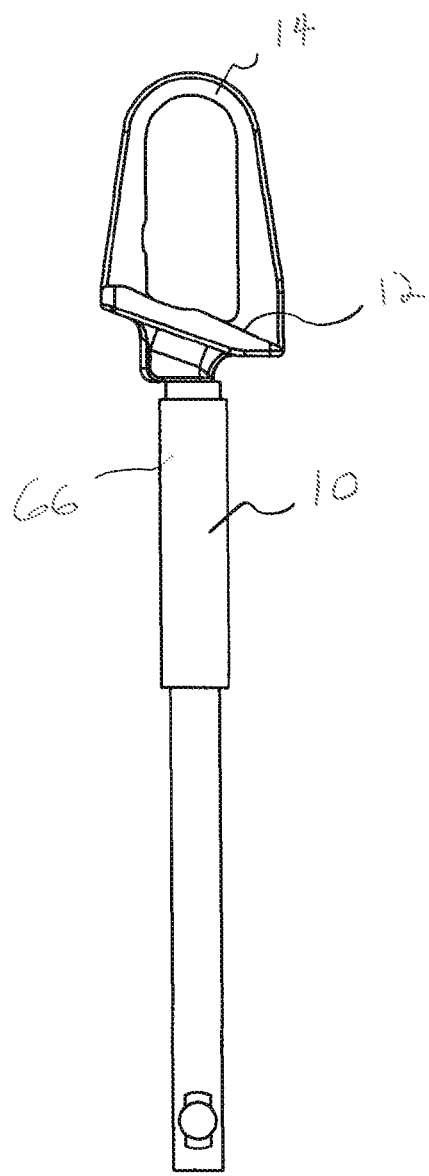
FIG. 9 is an elevational view of the inner body of FIG. 8 showing openings of the retention structures for receiving the locking mechanism.

The tensioning instrument includes a body assembly 9 having a support, such as inner body 10, which is slidably connected to a guide, such as guide tube 22, and a biasing member, such as spring 26, disposed between the body 10 and the guide tube 22, as shown in FIG. 6. In one form, the guide tube 22 acts as a pedestal for one end of the spring 26 and the body 10 has a seat connected thereto which engages the other end of the spring 26. The body 10 has an axial shaft 17 having an opening 17A sized to receive a pin 19 which is fixed to the shaft 17. Both the shaft 17 and the pin 19 have through openings 47, 21 sized to permit the cable 40 to pass therethrough (see FIG. 4). The guide tube 22 has a slot 25 in which the pin 19 is captured so that the pin 19 slides along the slot 25 as the body 10 moves axially relative to the guide tube 22. The engagement of the body pin 19 and the guide tube slot 25 restricts the body 10 to axial movement relative to the guide tube 22. The body shaft 17, guide tube 22, and pin 19/slot 25 assembly is preferably configured so that the spring 26 is under slight compression when the instrument is assembled, as shown in FIGS. 1-5.

With reference to FIG. 6, the distal end portion of the instrument 5 includes a tip member 91 that is partially received within the tubular guide 22 a distal tip 24 for engaging the cable connector 42. The tip member 91 also has a slot 93 that is aligned with the slot 25 of the tubular guide 22 once the tip member 91 has been assembled with the tubular guide 22. As shown in FIGS. 4 and 5, the pin 19 of the body 10 is slidable along the aligned slots 25, 93 when the instrument 5 is assembled.

With the distal tip 24 of the instrument 5 abutting the cable connector 42 (see FIG. 12), the lever 28 may be pivoted about an axis 35 (see FIG. 4) to shift the body 10 toward the guide tube 22 and compress the spring 26. Pivoting the cam lever 28 also causes the locking mechanism 30 to be reconfigured to a locked configuration which fixes the locking mechanism to the cable 40, wraps the cable 40 partly around a ring 72 of the locking mechanism 30, and moves the locking mechanism 30 away from the distal tip 24 to apply full tension. The lever 28 includes an engagement surface, such as cam surface 43 of cam 46, rigidly connected to the lever 28 that bears against an engagement surface of the body 10, such as follower surface 12, with pivoting of the lever 28 (see FIGS. 12-16). The camming engagement of the surfaces 43, 12 translates rotary movement of the lever 28 into axial movement of the body 10 which then compresses the spring 26.

Figure 15:
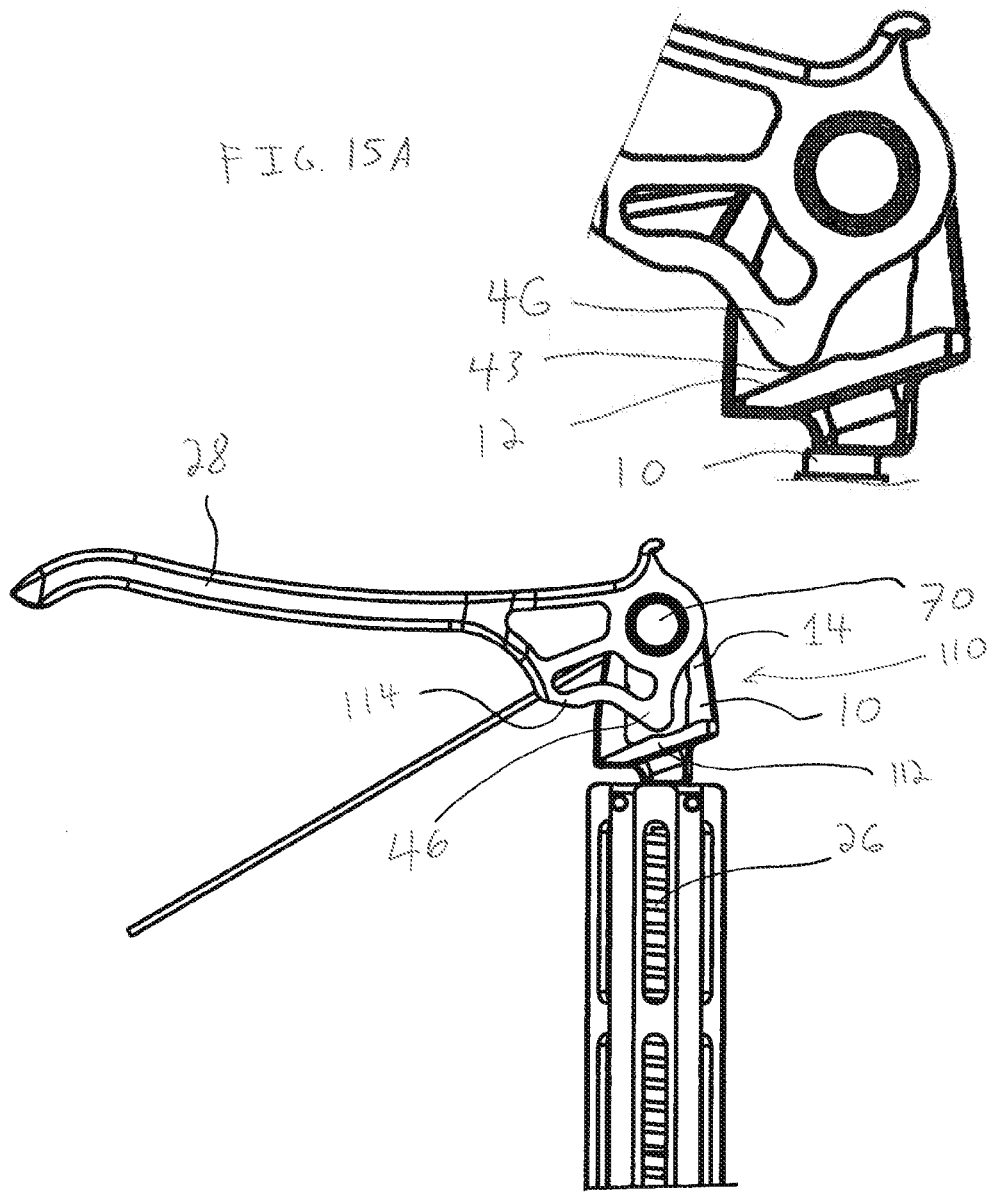
FIG. 15A is an enlarged partial view of the tensioning instrument of FIG. 14 showing a cam surface of the lever bearing against a follower surface of the inner body.
FIG. 15B is an enlarged partial view of the tensioning instrument of FIG. 12 showing the handle pivoted beyond an over-center position.
Figure 16:
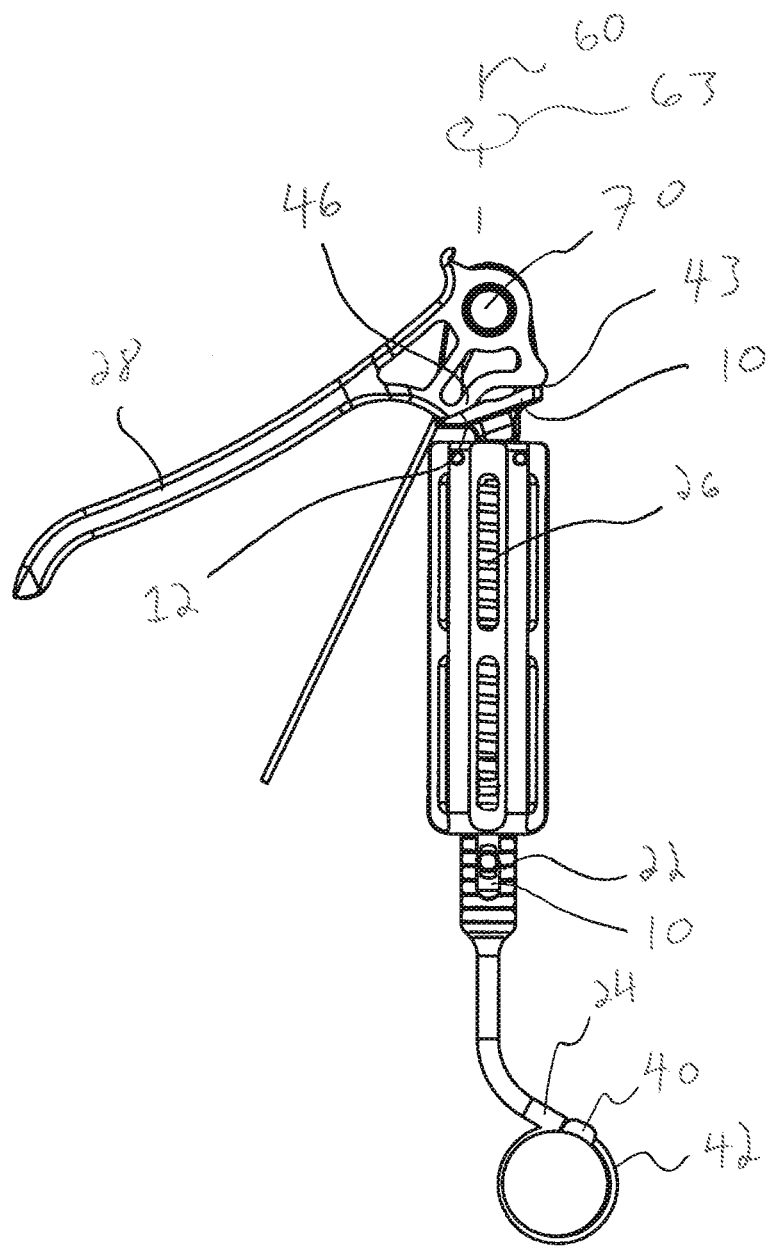
FIG. 16 is a schematic view of the tensioning instrument of FIG. 12 showing the handle pivoted to the locked position.

The tensioning mechanism 11 may include an over-center lock 110 comprising the lever 28 wherein pivoting the lever 28 beyond an over-center position (see FIG. 15) advances the cam member 46 beyond a catch 112 of the lock 110 which restricts pivoting of the lever 28 away from the locked position (see FIG. 16). The over-center lock 110 may also include a stop member 114 fixed to the cam member 46 and which abuts the follower surface 12 of the body 10 once the lever 28 has been pivoted to the locked position. Thus, both the stop member 114 and the cam member 46 are engaged with the follower surface 12 once the lever 28 has been pivoted to the locked position which restricts pivoting of the lever 28 away from its locked or beyond-center position.

To advance the cable 40 through the instrument 5, the cable 40 is routed axially and proximally through a passageway 45 of the tip 24, through the opening 21 of the pin 19, through the throughbore 47 of the body 10, through an aperture 48 of the locking mechanism 30, and out the rear of the instrument 5 past the lever 28 (see FIGS. 4 and 5). When the lever 28 is in an open or cable passage position, a shaft 70 and the ring 72 of the locking mechanism 30 are properly aligned with the throughbore 47 of the body 10, as shown in FIG. 5. This allows for passage of the cable 40 axially and proximally through the instrument 5.

The tensioning mechanism 11 moves the locking mechanism 30 a relatively short distance, e.g., approximately 1.25 inches, when compared to traditional tensioning instruments, but a user is able to apply a desired amount of tension on the cable 40 including a desired amount of preload using the tensioning handle 20 of the pretensioning mechanism 13. More specifically, the tensioning handle 20 can be adjusted to compress the spring 26 before, during, or after the lever 28 is pivoted between the open and locked positions.

The tensioning handle 20 may be threadingly engaged with the body 10 so that rotation of the handle 20 translates the handle 20 axially along the body 10 and compresses the spring 26 to apply a preload to the spring. More specifically, the spring 26 is located inside an interior 27 of the tensioning handle 20 and biases against a bushing 29A between the spring 26 and the tensioning handle 20 and also biases against a bushing 29B disposed between the spring 26 and the guide tube 22, as shown in FIGS. 4-6. In this manner, the spring 26 biases the tensioning handle 20 (and the body 10 threadingly engaged thereto) away from the guide tube 22.

The tensioning handle 20 has a collar 62 with threads 64 that engage a threaded portion 66 of the inner body 10 of the instrument (see FIG. 6). The threads 64 and the threaded portion 66 are configured such that rotating the tensioning handle 20 clockwise in direction 63 about axis 60 causes the tensioning handle to move downward in direction 65 along the threaded portion 66 of the body 10 and rotating the tensioning handle 20 counterclockwise about axis 60 causes the tensioning handle 20 to move upward in direction 66 along the threaded portion 66 of the body 10, as shown in FIG. 1. As the tension handle 20 is rotated clockwise from an initial, most proximal position along the threaded portion 66 (see FIG. 2), the spring 26 is compressed. With the locking mechanism 30 secured to the cable 40, compressing the spring 26 by rotating the handle 20 applies tension to the cable 40 due to the force from the spring 26 produced in response from its compression.

Figure 10:
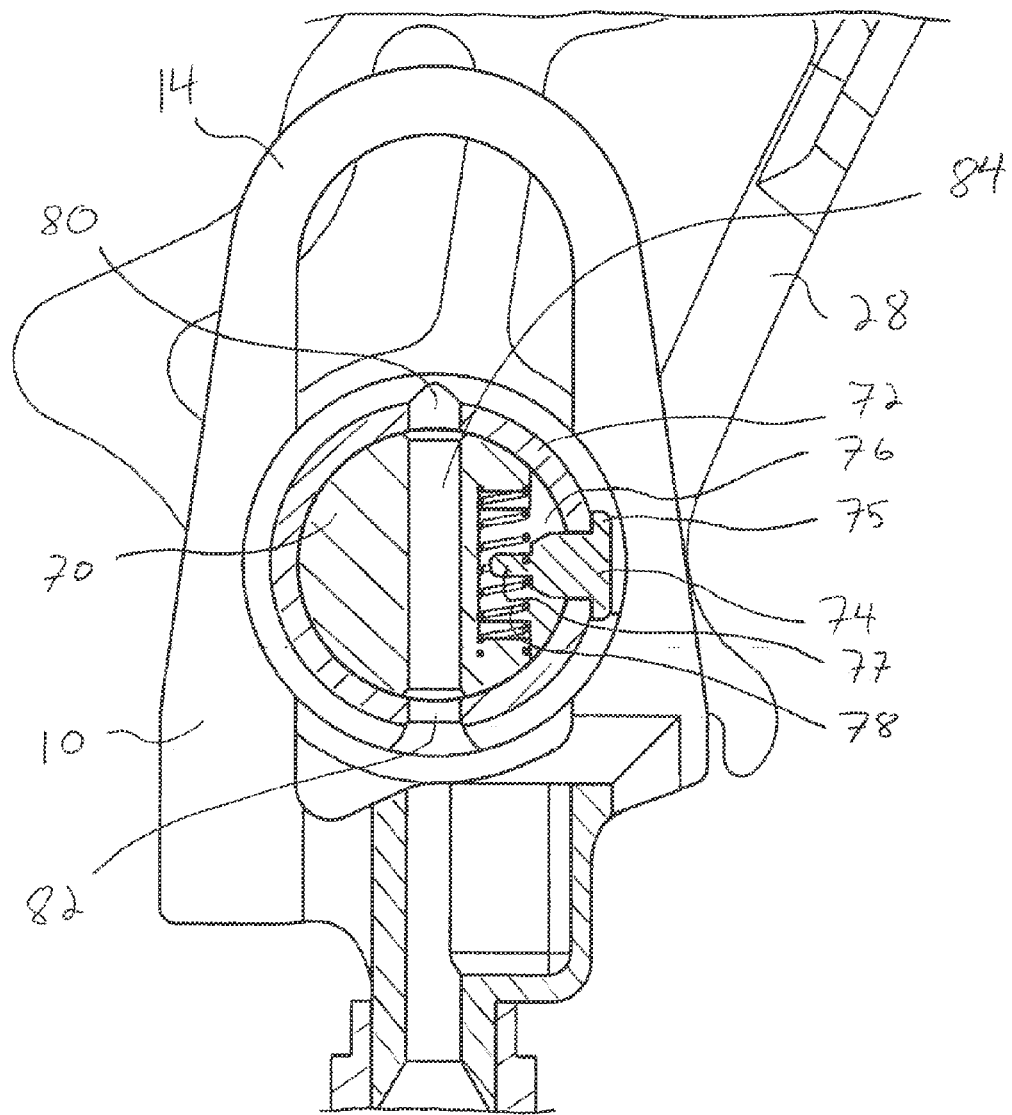
FIG. 10 is a cross-sectional view of the area in circle shown in the dash circle of FIG. 5 showing a shaft and a ring of the locking mechanism with openings of the shaft and ring aligned.
Figure 11:
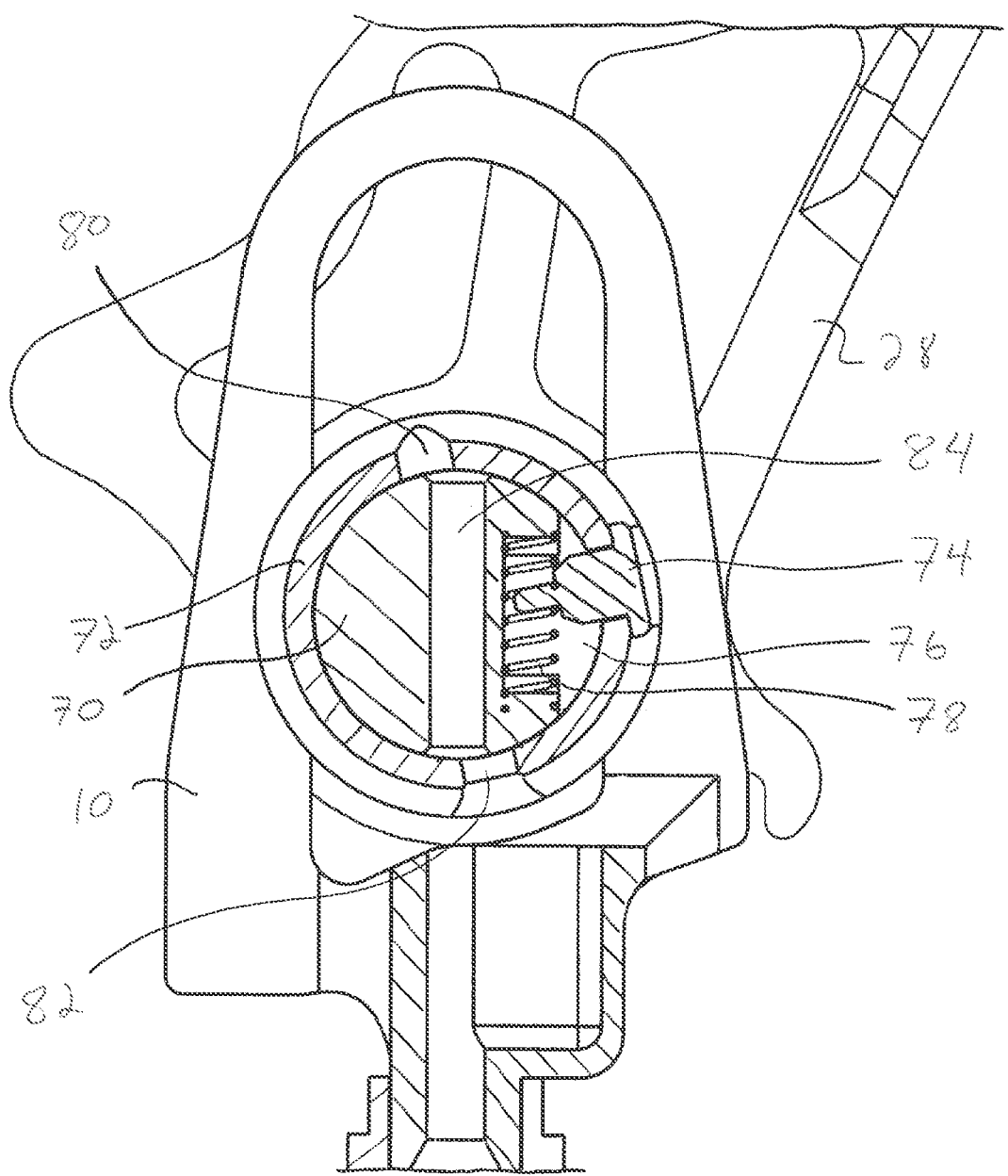
FIG. 11 is a cross-sectional view similar to FIG. 10 showing the ring shifted about the shaft and the resulting misalignment of the openings of the ring and shaft which secures a cable to the locking mechanism.

The shaft 70 is preferably rigidly connected to the lever 28 and the ring 72 is disposed on the shaft 70, as shown in FIGS. 6, 10, and 11. The shaft 70 and ring 72 have a limited amount of play therebetween that permits the ring 72 to shift about the circumference of the shaft 70, such as approximately 4 or 5 degrees, which may be seen by comparing FIGS. 10 and 11. The locking mechanism 30 includes a tooth 74 having a proximal end 75 fixed to the ring 72 and a distal end 77 extending into a recess 76 in the shaft 70 (see FIG. 6). The distal end 77 of the tooth 74 engages a spring 78 disposed in the recess 76 and held within the recess by the ring 72 extending about the shaft 70. Shifting the ring 72 about the circumference of the shaft 70 compresses the spring 78. The spring 78 then biases against the tooth 74 to shift the ring 72 back into a neutral position about the shaft 70. In the neutral position, radially extending openings 80, 82 in the ring 72 are aligned with a diametrically extending throughbore 84 of the shaft 70. The neutral position permits ready passage of an end of the cable 40 in an axial and proximal direction through the locking mechanism 30.

Figure 17:
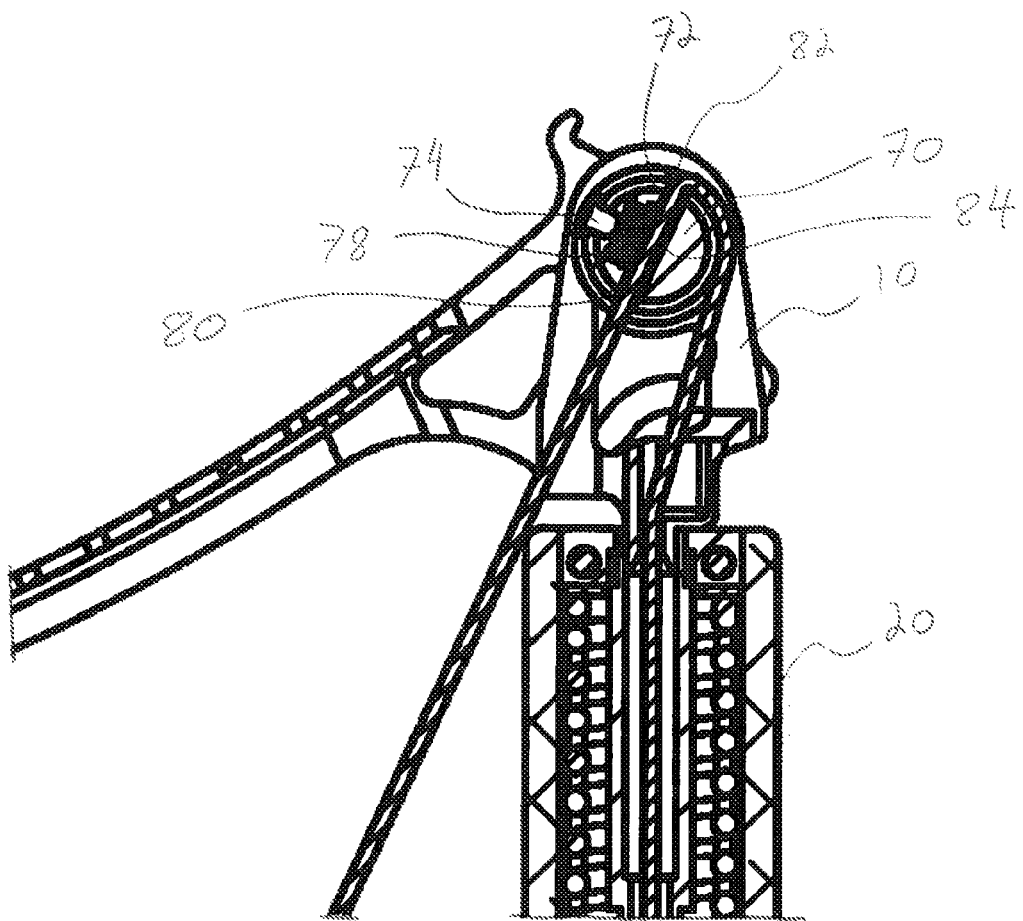
FIG. 17 is an enlarged cross-sectional view of the tensioning instrument of FIG. 16 showing the surgical cable wrapped partially around the ring of the locking mechanism due to pivoting of the handle.

When the lever 28 is pivoted towards the locked position, the shaft 70 and the ring 72 disposed thereon may pivot about an axis 35 to the position shown in FIG. 17. The tension in the cable 40 pulls on the ring 72 which shifts the ring 72 circumferentially about the shaft 70 and pinches the cable between the shaft 70 and the ring 72 at two places, i.e., at the intersections of the ring openings 80, 82 and the shaft aperture 84 (see FIG. 11).

As the lever 28 is pivoted to the fully locked position, the cam surface 43 cams against the follower surface 12 of the body 10 of the tensioning instrument (FIG. 15A) which shifts the lever 28 and the shaft 70 rigidly connected thereto away from the follower surface 12, shifts the body 10 distally, and compresses the spring 26. This shifting can be seen by comparing the lower position of the shaft 70 within hoops 14 of the body 10 in FIG. 12 (with the lever 28 in the open position) and the upper or higher position of the shaft 70 within hoops 14 of the body 10 in FIG. 16 (with the lever 28 in the locked position). Although pivoting the lever 28 shifts the locking mechanism 30 upward relative to the body 10, the body 10 shifts downward relative to the tip 24 due to the generally fixed length of the surgical cable 40 once the locking mechanism 30 has been secured to the cable 40. Pivoting the lever 28 also tensions the cable 40 by wrapping the cable 40 around the ring 72, as shown in FIG. 17.

In one approach, the rigid connection between the shaft 70 and the cam member 46 creates an effective lever arm between the shaft 70 and the cam member 46. Further, the cam member 46 may include a base portion 71 adjacent the shaft 70 and an engagement portion 73 extending away from the base portion 71 with the cam surface 43 disposed thereon. The cam surface 43 transmits torque applied to the shaft 70 as force against follower surface 12 of the body 10. This force shifts the body 10 toward the guide tube 22 and away from the locking mechanism 30 as the lever 28 is pivoted to the locked position. This movement of the body 10 can be seen by the lower position of the body 10 in FIG. 16 than in FIG. 12.

In addition to the rigid connection to the cam member 46, the lever 28 is also rigidly connected to the shaft 70 such that the lever 28 acts as a lever arm upon the shaft 70. In one approach, the mechanical advantage a user may apply to the cable 40 is a function of the length of the lever 28 to the distance between the shaft 70 and cam surface 43 which cams against follower surface 12 of the body 10.

The instrument 5 also has a scale 23 disposed on an outer surface of the guide tube 22. The scale 23 numerically shows how much tension is applied in the cable 40 based upon the position of the tensioning handle 20 along the tube 22. Pivoting the lever 28 from the open to the locked position engages the surfaces 43, 12 of the lever 28 and guide tube 22 and shifts the body 10 axially toward the guide tube 22, as discussed above. Because the tensioning handle 20 is threading engaged with the body 20, the tensioning handle 20 also travels distally toward the guide tube 22 which compresses the spring 26 and tensions the cable 40 with pivoting of the lever 28 to the locked position. As will be appreciated, it takes a set amount of force to move the spring 26 a set distance and this force is shown in the scale 23 for example, as a percentage amount of tension, custom scale or as a linear force description. Stated differently, moving the body 10 (and handle 20 connected thereto) to compress the spring 26 a distance and apply a tension the cable 40 involves moving the handle 20 a set distance along the outer surface of the guide tube 22. Thus, the position of the handle 20 along the scale 23 on the guide tube 22 is correlated to the compression of the spring 26 and the resulting tension in the cable 20.

With reference to FIGS. 12-17, a method of using the tensioning instrument 5 to apply tension to a cerclage cable construct 6 will now be described. Initially, on an operating room back table prior to surgery, a surgeon may need to perform the following process to determine his/her desired tension level. First, rotate the tensioning handle 20 counterclockwise about the longitudinal axis 60 of the instrument 5 until the tensioning handle 20 reaches a maximum upper position relative to the scale 23 to set the tension on the spring 26 to a minimum value, such as zero newtons (0 N), as shown in FIG. 12.

Figure 14:
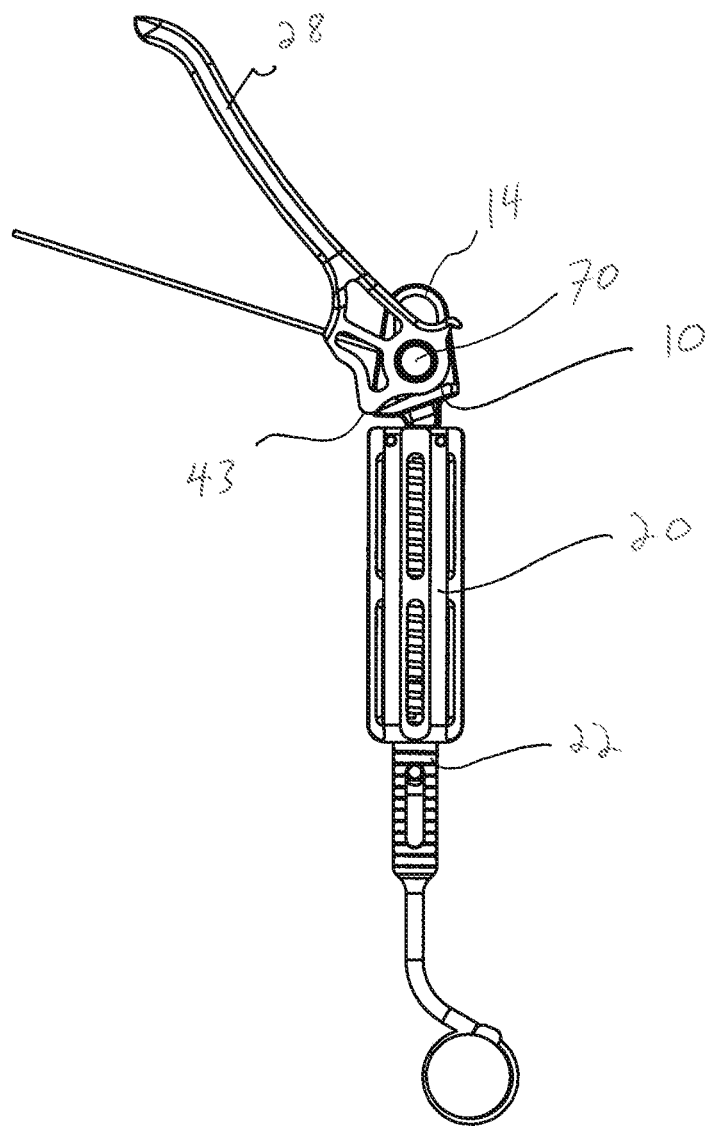
FIG. 14 is a schematic view similar to FIG. 12 showing the lever pivoted away from the unlocked position.

Next, create a test cerclage construct 6 by routing a free end of the cable 40 around an object (e.g., a simulator or bone 8) and through the connector 42. Pass the cable 40 axially and proximally through the tensioning instrument 5 from the tip 24 and out the locking mechanism 30 adjacent the handle 28, as shown in FIG. 12. Remove all slack in the cable 40 by simultaneously pulling in direction 100 on a free end 102 of the cable 40 and pushing the tensioning instrument 5 in direction 104 toward the cerclage connector 42. Pivot the lever 28 fully toward the locked position to automatically lock the cable 40 in the locking mechanism 30, shift the locking mechanism 30 upward relative to the body 10 of the instrument due to the camming engagement of surfaces 43, 12, and apply a predetermined, minimum tension to the surgical cable 40, as shown in FIGS. 14-16. The minimum tension is produced by the compression of the spring 26 due to the shifting of the body 10 toward the guide tube 22 and the shifting of the locking mechanism 30 away from the guide tube 22, as discussed above. For example, this predetermined, minimum tension may be forty newtons (40 N). If this amount of tension in the cable 40 measured from the scale 23 is sufficient, the surgeon may then connect the calibrated tensioning instrument 5 to the cable 40 that is to be tensioned in the patient. The surgeon then simply pivots the lever 28 from the open to the locked position which fixes the locking mechanism 30 to the surgical cable 40 and applies the predetermined, minimum tension of 40 N.

Figure 18:
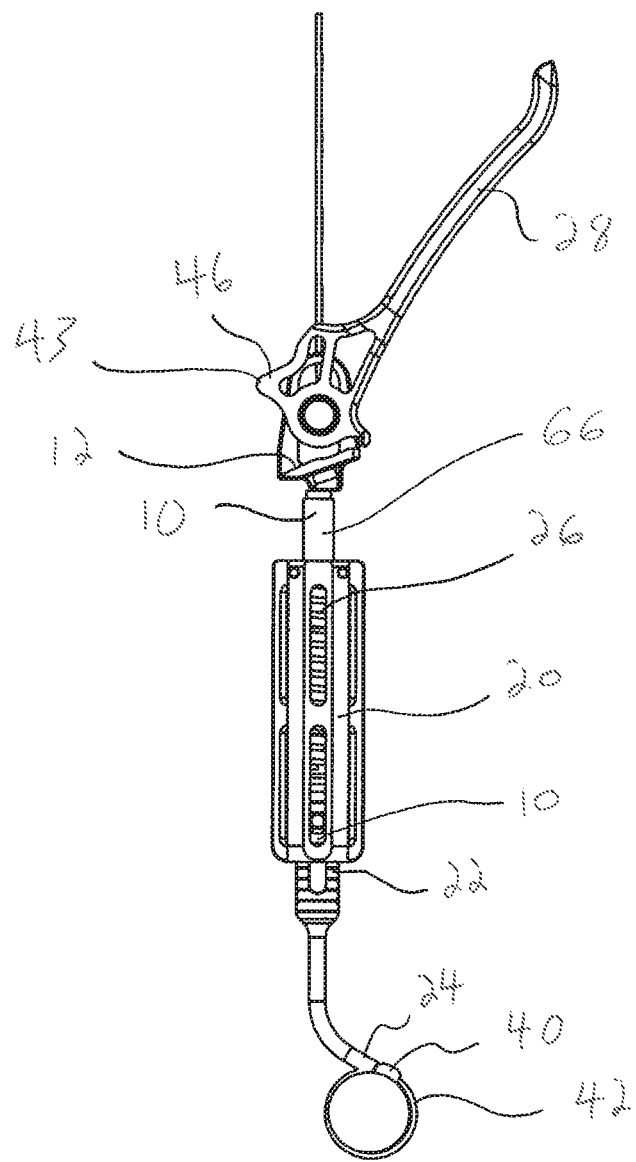
FIG. 18 is a schematic view similar to FIG. 12 showing a tensioning handle of the tensioning instrument shifted distally to pretension a spring within the tensioning instrument.
Figure 19:
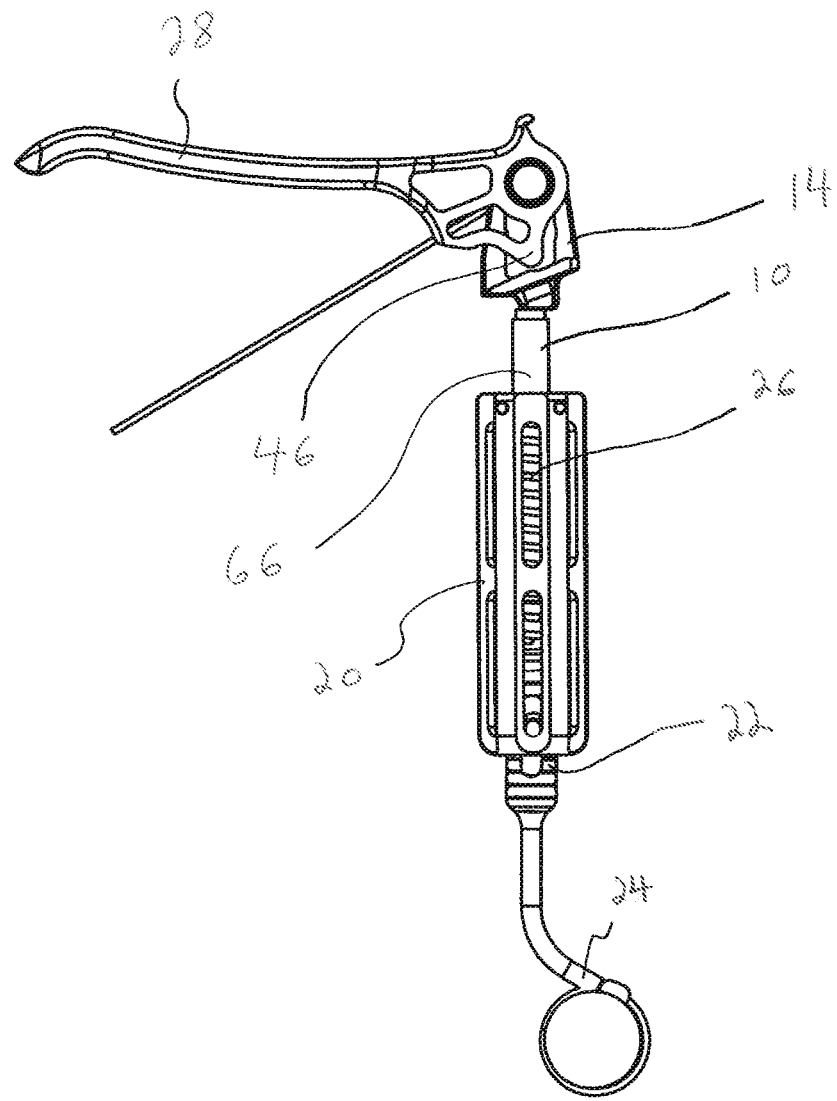
FIG. 19 is a schematic view of the tensioning instrument of FIG. 18 showing the lever pivoted away from the open position and the cam surface of the lever bearing against the follower surface of the support.
Figure 20:
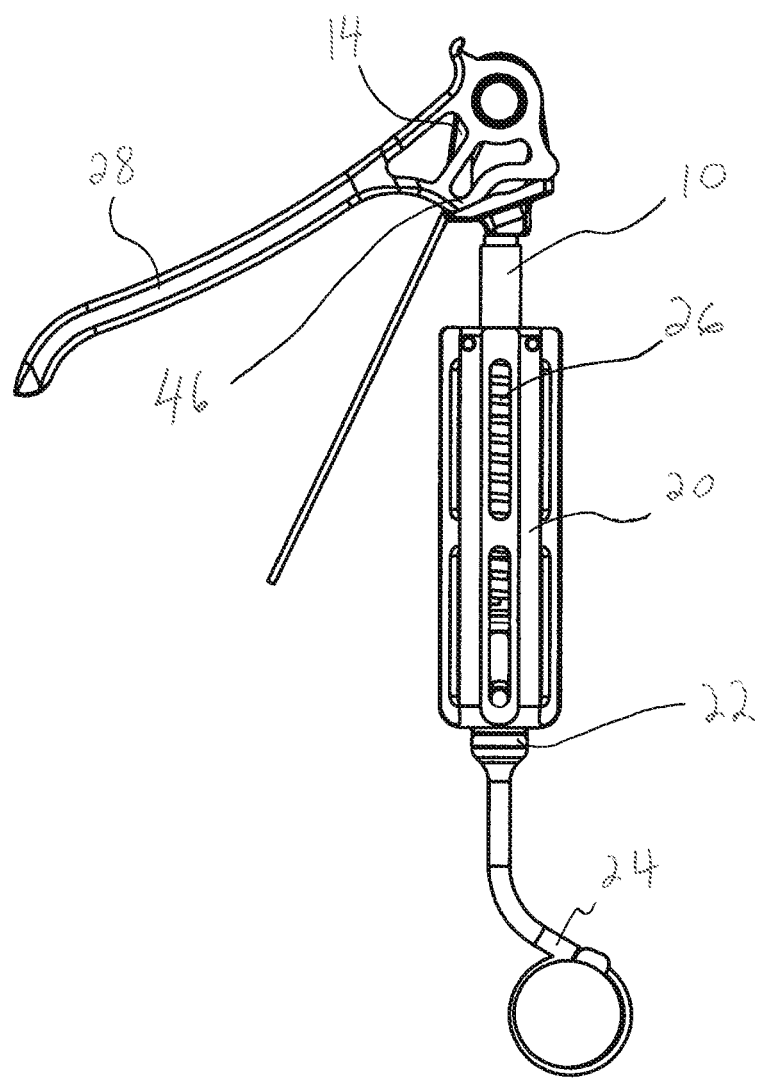
FIG. 20 is a schematic view of the tensioning instrument of FIG. 18 showing the lever pivoted to the locked position.

With reference to FIG. 16, if the surgeon desires a greater amount of tension to be applied to the cable 40 than the minimum amount, the surgeon may rotate the tensioning handle 20 clockwise about the longitudinal axis 60 to move the tensioning handle 20 downward along the body 10 and the guide tube 22 to a preloading position (see relative position of body 10 and handle 20 in FIG. 18). Due to the threaded engagement between the tensioning handle 20 and the body 10, rotating the tensioning handle 20 creates relative movement between the tensioning handle 20 and the body 10 which tends to shift the body 10 upward away from the tip 24 and tends to shift the tensioning handle 20 downward toward the tip 24. Because the cable 40 generally does not elongate under tension, the distance between the body 10 (and locking mechanism 30 received therein) and the tip 24 of the instrument is generally fixed once the lever 28 has been pivoted to the locked position to lock the locking mechanism 30 onto the cable 40, as shown in FIG. 16. Thus, rotating the tensioning handle 20 in direction 63 about the longitudinal axis 60 does not significantly move the body 10 relative to the tip 24 with the lever 28 in the locked position. The spring 26, however, compresses to permit downward movement of the tensioning handle 20 as the tensioning handle 20 is rotated clockwise in direction 63. This permits relative movement between the tensioning handle 20 and the body 10 as the tensioning handle 20 is rotated in direction 63.

Rotating the tensioning handle 20 clockwise in direction 63 about the axis 60 and the concurrent downward movement of the tensioning handle 20 toward the tip 24 of the instrument compresses the spring 26 which, in turn, biases against the downwardly moving tensioning handle 20. Because the tensioning handle 20 is threadingly engaged with the threaded portion 66 of the body 10, the biasing force from the spring 26 is transmitted to the body 20.

The upward biasing force from the spring 26 is then transferred to the locking mechanism 30 via the engagement between the cam 46 and the follower surface 12 of the body 10. Because the cam member 46 (and the locking mechanism 30 connected thereto) is fixed to the cable 40, the upward biasing force from the spring 26 is transmitted to the cable 40 which, in turn, tensions the cable 40. In sum, rotating the tensioning handle 20 in a clockwise, cable tensioning direction 63 moves the tensioning handle 20 toward the tip 24 of the instrument, compresses the spring 26, and applies preload tension to the cable 40.

While rotating the tensioning handle 20, the surgeon should evaluate the amount of tension in the cable 40. Once the desired amount of tension is reached, pivot the lever 28 to the unlocked position and record the scale value. With reference to FIG. 18, the instrument 5 is shown after the tensioning handle 20 has been rotated in direction 63 to apply a pre-load to the spring 26 and the lever 28 has been pivoted to the open position. The scale value can be recorded by visually identifying the position of the tensioning handle 20 along the scale 23 (see FIGS. 12 and 18 for different scale values).

With the desired pretension value determined and set by the position of the tensioning handle 20, the pretensioned instrument 5 may be used to tension an in-vitro cerclage cable 40 to a desired final tension. Specifically, the surgeon routes a free end of the cable 40 into the tensioning instrument tip 24, axially and proximally through the instrument 5, and out the locking mechanism 30. The free end of the cable 40 is pulled away from the cerclage connector 42 and the instrument 5 is pushed toward the connector 42 to engage the instrument tip 24 with the connector 42 and remove all slack in the cable 42. Next, pivot the lever 28 from the open position to the locked position to lock the cable 40 in the locking mechanism and apply both the baseline, minimum tension and the pretension amount added by previously rotating the tensioning handle 20 to the desired pre-tension value. Stated differently, pivoting the lever 28 increases the tension in the cable 40 in excess of the pretensioning tension applied to achieve a desired final tension. This tensions the cable 40 to the desired final tension simply by pivoting the lever 28 from the open position to the locked position.

In some surgeries, multiple tensioning instruments 5 are used for multiple cerclage cable constructs and it may be desirable for all of the tensioning instruments to apply a desired tension to the cables 40. In these applications, the additional tensioning instruments 5 are manipulated to adjust their tensioning handles 20 to match the pretension value of the first tensioning instrument 5 determined on the operating room back table prior to surgery. With all of the tensioning instruments 5 set for the desired pretension, the surgeon can route a cable 40 axially and proximally through each one of the tensioning instruments 5, remove the cable slack, and pivot the lever 28 fully to apply the full desired amount of tension to the cable 40. This allows each tensioning instrument 5 to apply approximately the same amount of tension to each of the cables 40 simply by connecting the pretensioned instruments to the cables 5 and pivoting the levers 28. Should more or less tension be desired for one of the cables 40, rotate the tensioning handle 20 of the respective tensioning device 5 clockwise or counterclockwise about the longitudinal axis 60 without unlocking the lever 28. Further, if only the minimum, predetermined amount of tension is desired, i.e., without any pretension load, the handles 20 of the instruments 5 may all be set to their minimum preload positions before the instruments 5 are connected to the cables 40. The levers 28 would then be pivoted to apply the minimum, predetermined amount of tension to each of the cables 40.

The tensioning instrument 5 provides a cost-effective solution to these multiple tensioning instrument applications because the individual components making up the tensioning instrument 5 have been configured for light weight and to minimize their cost. Thus, a surgical set of tensioning instruments 5 can be provided for lower cost than multiple traditional cable tensioning instruments.

The components of the tensioning instrument 5 may be made of variety of materials such as metals, alloys, and polymers. In one form, the components of the instrument 5 are made of stainless steel and/or aluminum.

Those skilled in the art would recognize that a wide variety of modifications, alterations, and combinations can be made with respect to the above described embodiments without departure from the spirit and scope of the invention, in that such modifications, alterations, and combinations, are to be viewed as being within the scope of the invention.

What is claimed is:

1. A tensioning instrument for tensioning a cable, the tensioning instrument comprising:
a pretensioner including a pretensioner actuator operable to be shifted for setting a selected level of tension for being applied to either an untensioned or tensioned cable; and
a tensioner including a tensioner actuator different from the pretensioner actuator and being operable to be shifted between unlocked and locked positions to cause the tensioner to apply the selected level of tension set by the pretensioner and to apply a predetermined amount of tension to the cable irrespective of the selected level of tension set by the pretensioner so that shifting the tensioner actuator from the unlocked position to the locked position causes the tensioner to increase the tension in the cable to the sum of the selected level of tension and the predetermined amount of tension.

2. The tensioning instrument of claim 1 wherein the tensioner actuator includes an elongate lever pivotal between the unlocked and locked positions.

3. The tensioning instrument of claim 1 wherein the pretensioner actuator is movable between a first position where the selected level of tension is a nominal amount and a second position where the selected tension is greater than the nominal amount and, with the tensioner actuator in the locked position and the cable tensioned, the pretensioner actuator is operable to increase the tension in the cable by movement of the pretensioner actuator toward the second position.

4. The tensioning instrument of claim 1 wherein the tensioning instrument has a longitudinal axis and the pretensioner actuator is rotatable about the longitudinal axis to move the pretensioner actuator between an initial position and a preloading position to increase the selected level of tension for being applied to the cable.

5. The tensioning instrument of claim 4 wherein the tensioner actuator is pivotal about a pivot axis extending transverse to the longitudinal axis of the tensioning instrument.

6. The tensioning instrument of claim 1 wherein the tensioner includes a biasing member that is compressed with movement of the tensioner actuator between the unlocked and locked positions and the pretensioner actuator is configured to compress the biasing member with shifting of the pretensioner actuator between initial and preloading positions thereof.

7. A tensioning instrument for tensioning a cable, the tensioning instrument comprising:
a pretensioning mechanism configured to allow a predetermined preload tension to be applied to the cable;

a tensioning mechanism operable to increase the tension in cable by a predetermined amount in excess of the preload tension applied by the pretensioning mechanism;
a first actuator operatively coupled to the pretensioning mechanism and configured to be moved between an initial position where the predetermined preload tension applied to the cable by the pretensioning mechanism is a nominal amount and a preloading position where the predetermined preloading tension applied by the pretensioning mechanism is greater than the nominal amount;
a second actuator different from the first actuator that is operatively coupled to the tensioning mechanism and movable between an open position and a locked position to cause the tensioning mechanism to increase the tension in the cable by the predetermined amount in excess of the preload tension;
wherein the tensioning mechanism comprises an over-center lock connected to the second actuator, the over-center lock being configured so that movement of the second actuator to the locked position shifts the lock beyond center and restricts the tensioning mechanism from releasing tension in the cable.

8. A tensioning instrument for tensioning a cable, the tensioning instrument comprising:
a pretensioning mechanism configured to allow a predetermined preload tension to be applied to the cable;
a tensioning mechanism operable to increase the tension in cable by a predetermined amount in excess of the preload tension applied by the pretensioning mechanism;
a first actuator operatively coupled to the pretensioning mechanism and configured to be moved between an initial position where the predetermined preload tension applied to the cable by the pretensioning mechanism is a nominal amount and a preloading position where the predetermined preloading tension applied by the pretensioning mechanism is greater than the nominal amount;
a second actuator different from the first actuator that is operatively coupled to the tensioning mechanism and movable between an open position and a locked position to cause the tensioning mechanism to increase the tension in the cable by the predetermined amount in excess of the preload tension;
wherein the tensioning mechanism includes a locking device having an unlocked configuration that permits the cable to be connected to the locking device and a locked configuration which fixes the cable to the locking device.

9. A tensioning instrument comprising:
a body assembly having a distal end portion and a proximal end portion, the body assembly having a longitudinal axis extending between the distal and proximal end portions;
a guide of the body assembly adjacent the distal end portion;
a support of the body assembly slidably movable along the axis;
a biasing member between the guide and the support, the biasing member configured to bias the support away from the guide along the longitudinal axis of the body assembly;
a locking mechanism carried on the support and axially movable relative to the support, the locking mechanism having an unlocked configuration which permits a cable to be connected to the locking mechanism and a locked configuration which fixes the cable to the locking mechanism;
an actuator connected to the locking mechanism and pivotal relative to the support between an open position and a locked position; and
engagement surfaces of the actuator and support configured to engage with pivoting of the actuator between the open and locked positions and shift the support axially and distally toward the guide which compresses the biasing member and applies a tensioning force to the cable when the locking mechanism is fixed to the cable.

10. The tensioning instrument of claim 9 wherein the engagement surfaces of the actuator and guide include a curved cam surface and a generally straight follower surface extending obliquely to the longitudinal axis of the body assembly.

11. The tensioning instrument of claim 9 wherein the actuator is rigidly connected to the locking mechanism; and
a pivot connection between the locking mechanism and the support which permits the locking mechanism to pivot relative to the support with pivoting of the actuator between the open and locked positions.

12. The tensioning instrument of claim 11 wherein the locking mechanism has an aperture sized to receive the cable and is aligned with the longitudinal axis of the body assembly with the actuator in the open position and pivoting of the actuator between the open and locked positions pivots the locking mechanism aperture out of alignment with the longitudinal axis and fixes the locking mechanism to the cable.

13. The tensioning instrument of claim 9 further comprising a pretensioner assembly connected to the support and having a seat engaged with the biasing member, the pretensioner assembly being axially shiftable along the support such that shifting the pretensioner assembly toward the guide compresses the biasing member.

14. The tensioning instrument of claim 9 wherein the actuator has a base portion connected to the locking mechanism and an engagement portion extending away from the base portion, the engagement portion having the engagement surface disposed thereon and a stop surface spaced from the engagement surface along the engagement portion with the engagement and stop surfaces both configured to abut the support when the actuator is pivoted to the locked position which restricts pivoting of the actuator away from the locked position.

15. The tensioning instrument of claim 9 wherein the locking mechanism comprises:
a shaft connected to the actuator and having a through opening; and
a ring disposed on the shaft and having at least one through opening which can be aligned with the through opening of the shaft, the ring being slidable about the shaft so that pivoting of the actuator while the cable extends through the shaft and ring openings causes a misalignment of the openings which fixes the shaft and ring to the cable.

16. The tensioning instrument of claim 9 wherein the support has an axial alignment shaft and a pin extending transversely thereto and the guide comprises:
an axial throughbore sized to receive the alignment shaft of the support;
a sidewall disposed about the axial throughbore; and
an axially elongated slot in the sidewall configured to receive the pin of the support and restrict movement of the support to axial movement relative to the guide.

17. The tensioning instrument of claim 16 wherein the guide includes indicia disposed on an outer surface of the sidewall; and
a handle connected to the support having a distal end portion disposed about the outer surface of the sidewall and movable therealong with shifting of the support toward the distal end portion such that the tension in the cable may be determined from the position of handle distal end portion along the guide sidewall outer surface.

18. The tensioning instrument of claim 9 wherein the support includes a retention structure having an opening elongated along the longitudinal axis of the body assembly and the locking mechanism includes a shaft received in the elongated opening such that the support retention structure maintains the locking mechanism on the support while permitting axial movement of the locking mechanism.

19. The tensioning instrument of claim 7 wherein the tensioning instrument has a longitudinal axis and the first actuator is rotatable about the longitudinal axis to move the first actuator between the initial position and the preloading position.

20. The tensioning instrument of claim 19 wherein the second actuator is pivotal about a pivot axis extending transverse to the longitudinal axis of the tensioning instrument.

21. The tensioning instrument of claim 7 wherein the tensioning mechanism includes a biasing member that is compressed with movement of the second actuator between the open and locked positions and the first actuator is configured to compress the biasing member with movement of the first actuator between the initial and preloading positions.

22. The tensioning instrument of claim 7 wherein the tensioning mechanism includes a locking device having an unlocked configuration that permits the cable to be connected to the locking device and a locked configuration which fixes the cable to the locking device.

23. The tensioning instrument of claim 7 wherein the second actuator includes an elongate lever pivotal between the open and locked positions.

24. The tensioning instrument of claim 8 wherein the tensioning instrument has a longitudinal axis and the first actuator is rotatable about the longitudinal axis to move the first actuator between the initial position and the preloading position.

25. The tensioning instrument of claim 24 wherein the second actuator is pivotal about a pivot axis extending transverse to the longitudinal axis of the tensioning instrument.

26. The tensioning instrument of claim 8 wherein the tensioning mechanism includes a biasing member that is compressed with movement of the second actuator between the open and locked positions and the first actuator is configured to compress the biasing member with movement of the first actuator between the initial and preloading positions.

27. The tensioning instrument of claim 8 wherein the locking mechanism comprises:
 a shaft connected to the second actuator and having a through opening; and
 a ring disposed on the shaft and having at least one through opening which can be aligned with the through opening of the shaft, the ring being slidable about the shaft so that pivoting of the second actuator while the cable extends through the shaft and ring openings causes a misalignment of the openings which fixes the shaft and ring to the cable.

* * * * *